(12) United States Patent
Li et al.

(10) Patent No.: US 8,217,179 B2
(45) Date of Patent: Jul. 10, 2012

(54) PREPARATION METHOD OF PHENYLCARBOXAMIDES

(75) Inventors: Bin Li, Shenyang (CN); Hongfei Wu, Shenyang (CN); Haibo Yu, Shenyang (CN); Huibin Yang, Shenyang (CN)

(73) Assignees: Sinochem Corporation, Beijing (CN); Shenyang Research Institute of Chemical Industry Co., Ltd., Shenyang (CN)

( * ) Notice: Subject to any disclaimer, the term of this patent is extended or adjusted under 35 U.S.C. 154(b) by 205 days.

(21) Appl. No.: 12/918,133

(22) PCT Filed: Mar. 30, 2009

(86) PCT No.: PCT/CN2009/071072
§ 371 (c)(1),
(2), (4) Date: Aug. 18, 2010

(87) PCT Pub. No.: WO2009/121288
PCT Pub. Date: Oct. 8, 2009

(65) Prior Publication Data
US 2010/0317864 A1      Dec. 16, 2010

(30) Foreign Application Priority Data

Apr. 1, 2008  (CN) .......................... 2008 1 0103211

(51) Int. Cl.
*C07D 401/04*     (2006.01)
(52) U.S. Cl. .................................... 546/275.4
(58) Field of Classification Search ................ 546/275.4
See application file for complete search history.

(56) References Cited

U.S. PATENT DOCUMENTS 7,211,270 B2 * 5/2007 Lahm et al ..................... 424/405

OTHER PUBLICATIONS

English Translation of International Search Report mailed in PCT/CN2009/071072 on Jul. 23, 2009.

* cited by examiner

*Primary Examiner* — Patricia Morris
(74) *Attorney, Agent, or Firm* — Smith, Gambrell & Russell, LLP

(57) ABSTRACT

A preparation method of phenylcarboxamides of formula (I), the reaction scheme of which is as follows:

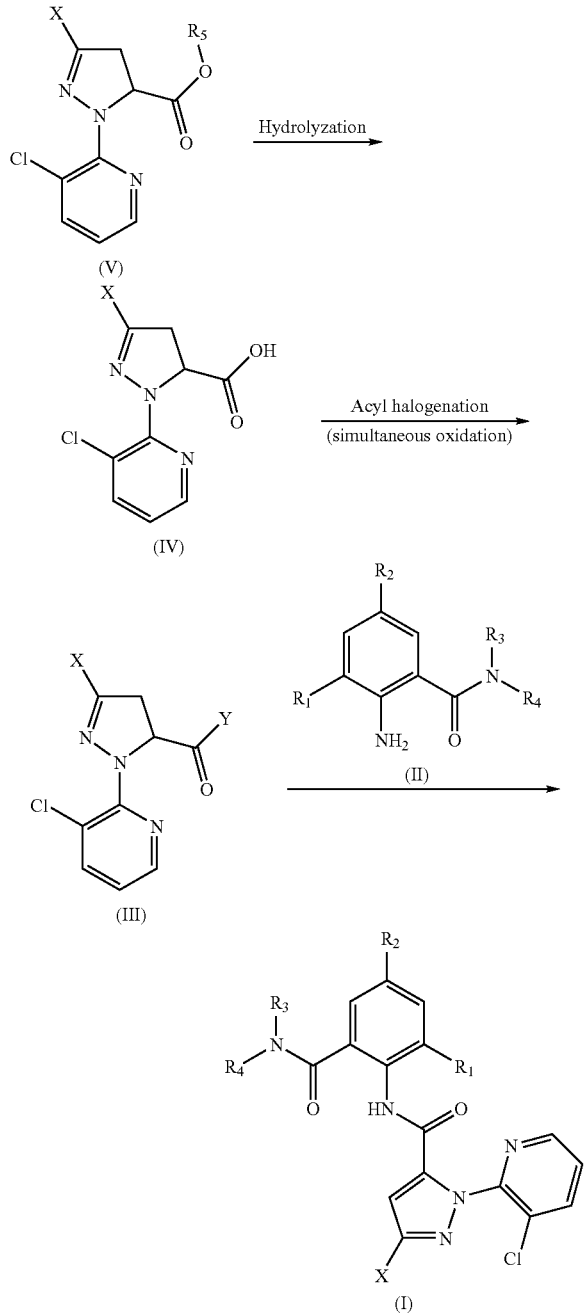

wherein the groups are defined in the description. In this method, 3-halo-1-(3-chloro-2-pyridinyl)-4,5-dihydro-1H-pyrazole-5-carboxylic acid esters (V) as the raw materials are hydrolyzed to obtain carboxylic acids of formula (IV) under a basic condition, and carboxylic acids (IV) are simultaneously acyl halogenated and oxidated to get acyl halide of formula (III), and then without the presence of a acid binging agent, acyl chlorides (III) are reacted with substituted anilines (II) to get phenylcarboxamides of formula (I) in high yield.

6 Claims, No Drawings

PREPARATION METHOD OF PHENYLCARBOXAMIDES

FIELD OF THE INVENTION

This invention belongs to the field of organic synthesis, and specifically relates to the preparation method of phenylcarboxamides.

BACKGROUND OF THE INVENTION

Phenylcarboxamides are a kind of novel insecticides with high efficacy and safety. 3-Bromo-N-(4-chloro-2-methyl-6-(methylcarbamoyl)phenyl)-1-(3-chloro-2-pyridyl)-1H-pyrazole-5-carboxamide is highly effective against insects, which is commercialized by DuPont, its generic common name is chlorantraniliprole; 3-Bromo-1-(3-chloropyridin-2-yl)-N-(4-cyano-2-methyl-6-(methylcarbamoyl)phenyl)-1H-pyrazole-5-carboxamide in development is highly effective against insects too, whose common name is cyantraniliprole.

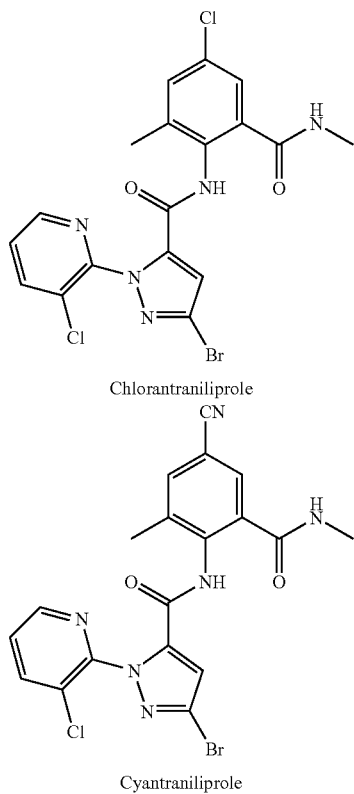

Chlorantraniliprole

Cyantraniliprole

There are a number of methods reported for preparing phenylcarboxamides, for example:

WO03/015519 A1 discloses that 3-halo-1-(3-chloro-2-pyridyl)-1H-pyrazole-5-carboxylic acids reacts with substituted anthranilic acids, in the presence of methanesulfonyl chloride and pyridine as acid binding agent to give the benzoxazinones in 86%-92% yield. Then the product reacts with the alkylamine to yield the phenylcarboxamides. Calculated by 3-halo-1-(3-chloro-2-pyridyl)-1H-pyrazole-5-carboxylic acids, the total yield of the two-steps is 58%-65%. Bioorganic & Medicinal Chemistry Letters, 17 (2007), 6274-6279 discloses that 3-halo-1-(3-chloro-2-pyridyl)-1H-pyrazole-5-carbonyl chlorides react with isatoic anhydrides to give the benzoxazinones in 23% yield.

WO2006/062978A1 discloses that 3-halo-1-(3-chloro-2-pyridyl)-1H-pyrazole-5-carboxylic acids react with substituted aminobenzamid, in the presence of methanesulfonyl chloride and 3-aminepyridine as acid binding agent to give the phenylcarboxamides and the dehydrated-cyclization byproduct, which can be converted into the target phenylcarboxamides under the reaction with hydrochloric acid. Calculated by 3-halo-1-(3-chloro-2-pyridyl)-1H-pyrazole-5-carboxylic acid, the crude yield under the best reaction conditions is 99.5% without mention of the product purity. The total yield is 88.4% after purified by recrystallization.

The methods for preparing 3-halo-1-(3-chloro-2-pyridyl)-4,5-dihydro-1H-pyrazole-5-carboxylates and 3-halo-1-(3-chloro-2-pyridyl)-1H-pyrazole-5-carbonyl chlorides have been disclosed by Bioorg. Med. Chem. Lett. 17 (2007), 6274-6279, WO03/015519 A1, and CN101298451. The 3-halo-1-(3-chloro-2-pyridyl)-1H-pyrazole-5-carboxylates can be prepared by the oxidation of 3-halo-1-(3-chloro-2-pyridyl)-4,5-dihydro-1H-pyrazole-5-carboxylates. They are hydrolyzed, and acyl chlorination into 3-halo-1-(3-chloro-2-pyridyl)-1H-pyrazole-5-carbonyl chlorides. The total yield of three-steps is 70%.

The researchers continuously make efforts to research and develop more advanced and favourable, and more environmentally friendly novel preparation methods, so as to manufacture the highly effective and safe phenylcarboxamide insecticides with higher quality and lower cost.

SUMMARY OF THE INVENTION

The purpose of this invention is to provide a novel method for preparing phenylcarboxamides, which is more concise and more environmentally friendly.

The phenylcarboxamides related to the present invention are a kind of new insecticides with high efficacy and safety. The inventors have done intensive exploration on their conventional preparation processes.

In the process of researching novel preparation methods, the inventors find unexpectedly that 3-halo-1-(3-chloro-2-pyridyl)-4,5-dihydro-1H-pyrazole-5-carboxylates can be hydrolyzed to 3-halo-1-(3-chloro-2-pyridyl)-4,5-dihydro-1H-pyrazole-5-carboxylic acids under basic conditions. They are disclosed previously that the acids could only be prepared by hydrolyzation of the corresponding esters under acidic conditions. However, the acids as represented by formula (IV) in the present invention have not been obtained practically.

The more unexpected results show that in the acyl halogenation of 3-halo-1-(3-chloro-2-pyridyl)-4,5-dihydro-1H-pyrazole-5-carboxylic acids with acyl halogenation reagents, meanwhile the pyrazoline ring can be oxidized to pyrazole ring. So 3-halo-1-(3-chloro-2-pyridyl)-1H-pyrazole-5-carbonyl halides can be prepared by acyl halogention and oxidation simultaneously. This novel method successfully avoids the conventional oxidation reaction with the use of oxidants, minimizes the reaction steps, reduces the environmental pollution, and increases the safety of the reactions.

This invention also relates to a method for preparing phenylcarboxamides employing 3-halo-1-(3-chloro-2-pyridyl)-1H-pyrazole-5-carbonyl halides to react with substituted anilines without the presence of acid binding agents in high yields. Thus, this invention provides a novel method for preparing phenylcarboxamides, and the technical embodiments of this invention are as follows:

A method for preparing phenylcarboxamides as represented by formula (I), the reaction scheme is as follows:

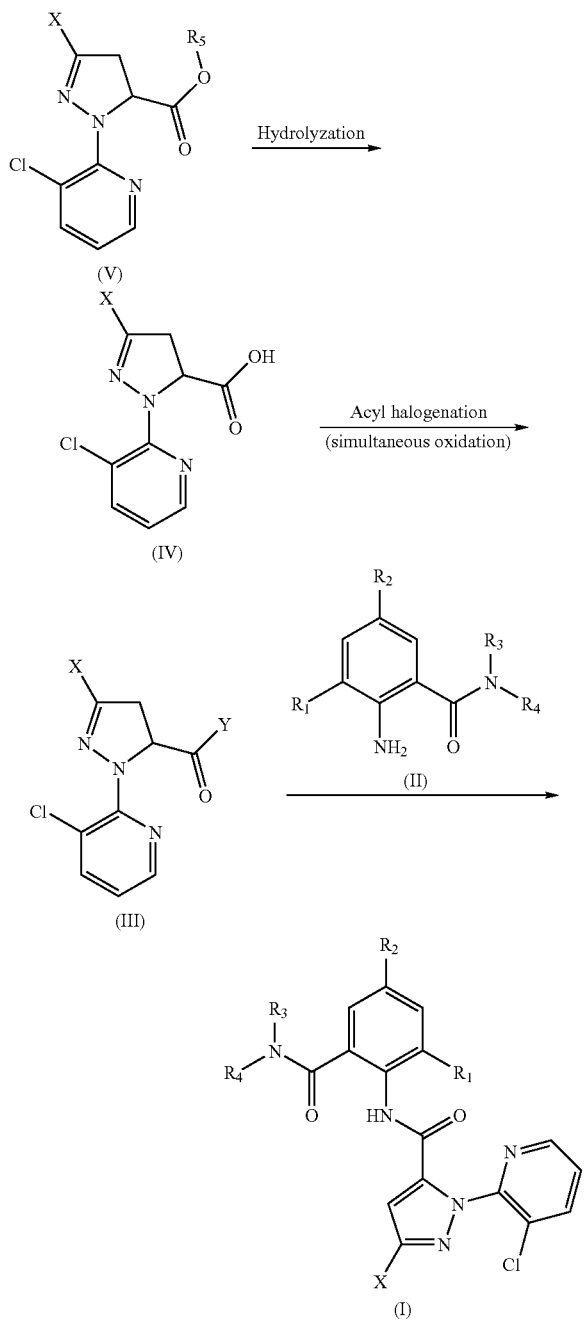

Wherein:

$R_1$ is halogen, CN or $CH_3$; $R_2$ is halogen or CN; $R_3$ is H or $C_1$-$C_3$ alkyl; $R_4$ is H, $C_1$-$C_6$ alkyl or $C_3$-$C_6$ cycloalkyl; $R_5$ is $C_1$-$C_{10}$ alkyl, benzyl or $C_3$-$C_5$ alkenyl; X and Y are selected independently Cl or Br.

These reactions include three steps as followed:

1) Hydrolysis reaction: the 3-halo-1-(3-chloro-2-pyridyl)-4,5-dihydro-1H-pyrazole-5-carboxylate (V) is added into 10 to 500 times moles solvent of water, the mixture of water and alcohol, or the mixture of water and ether, then add 0.8 to 2 times moles of base, at a temperature from −10° C. to boiling point for 0.5 to 48 hours. The carboxylic acid salt is formed, and then acidified to form the 3-halo-1-(3-chloro-2-pyridyl)-4,5-dihydro-1H-pyrazole-5-carboxylic acid of formula (IV).

When using the mixture of water and alcohol, or water and ether as solvent, the volume ratio of water to alcohol, or water to ether is 1:0.1-10.

The base in above hydrolysis reaction can be selected from the hydroxide or carbonate of the alkaline metal such as lithium, sodium or potassium. The acid used in the acidification is selected from hydrochloric acid or sulfuric acid. The carboxylic acid showed as formula (IV) can be isolated by the methods (including filtration, extraction, or distillation) known by the skilled person in the art.

2) Acyl halogenation and oxidation reaction: the carboxylic acid of formula (IV) react with 1 to 20 times moles acyl halide reagents in the appropriate solvent to obtain the 3-halo-1-(3-chloro-2-pyridyl)-1H-pyrazole-5-carbonyl halide of formula (III) at a temperature between −10° C. and boiling point for 0.5 to 48 hours for the acyl halogenation and oxidation reaction. The acyl halide reagent is selected from the group consisting of thionyl chloride, phosphorus trichloride, phosphorus tribromide, phosphorus pentachloride or phosphorus pentabromide. The solvent is selected from the group consisting of benzene, toluene, acetonitrile, dioxane, hexane or liquid acyl halide reagents, and the amount of solvent is 5 to 500 times moles that of the acid of formula (IV).

3) Condensation reaction: the acyl halide of formula (III) reacts with aniline (II), the molar ratio of the acyl halide of formula (III) to aniline (II) is 1:0.8-1.2, without the presence of acid binding agent in the appropriate solvent to obtain the phenylcarboxamide of formula (I) at a temperature between −10° C. and boiling point for 1 to 10 hours. The solvent is selected from the group consisting of dichloromethane, chloroform, carbon tetrachloride, hexane, benzene, toluene, ethyl acetate, acetonitrile, tetrahydrofuran, dioxane, acetone, butanone or dimethyl sulfoxide, and the amount of solvent is 5 to 500 times moles that of acyl halide of formula (III).

The preferred technical embodiments among above are as follows:

In the hydrolysis reaction, the molar ratio of the ester to base is 1:1-1.2. The temperature is between 10° C. and 50° C. And the reaction time is 0.5 to 2 hours. The solvent is selected from the mixture of water and alcohol, or the mixture of water and ether, and the volume ratio of water to alcohol, or water to ether is 1:0.5-1.5. The base is sodium hydroxide or potassium hydroxide.

In the acyl halogenation and oxidation process, the molar ratio of the acid of formula (IV) to acyl halide is 1:2-5. The temperature is between 50° C. and boiling point. The reaction time is 1 to 10 hours. The solvent is selected from the group consisting of benzene, toluene or hexane.

In the condensation reaction, the molar ratio of the acyl halide of formula (III) to the substituted aniline (II) is 1:0.9-1.1. The reaction temperature is between 20° C. and boiling point. The reaction time is 1 to 5 hours. The solvent is toluene or acetonitrile.

The preparation of substituted anilines (II) follows the methods described in WO03/015519A1.

The esters as formula (V) are prepared according to the following literature of WO03/015519A1, WO2008/072745A1 and WO2009/010260A2.

In above definitions of the formula compounds, the term "alkyl" indicates straight or branched alkyl such as methyl, ethyl, n-propyl, i-propyl, n-butyl, i-butyl, s-butyl, t-butyl, n-pentyl, i-pentyl, n-hexyl, etc. "Cycloalkyl" indicates ring of the link form, for example, cyclopropyl, cyclobutyl, cyclopentyl, cyclohexyl, methylcyclopropyl and cyclopropylcyclopropyl, etc. "Alkenyl" indicates straight or branched alkenyl such as 1-propenyl, 2-propenyl and different isomers of butenyl, pentenyl and hexenyl. "Alkenyl" also includes polyene such as 1,2-propydienyl and 2,4-hexadiene. "Halogen" includes fluorine, chlorine, bromine, and iodine.

Compared with the prior art, the novel method for preparing phenylcarboxamides, the method for preparing 3-halo-1-(3-chloro-2-pyridyl)-4,5-dihydro-1H-pyrazole-5-carboxylic acids, and the method for preparing 3-halo-1-(3-chloro-2-pyridyl)-1H-pyrazole-5-carbonyl halides provided in this invention are not only with unexpected high yield, but also more concise. Meanwhile, the by-product hydrochloric acid can be recycle used, the use of methanesulfonyl chloride and the acid binding agents such as organic tertiary amines can be avoided. So this method reduces the preparation cost, and it is more environmentally friendly.

It shall be noted that variations and changes are permitted within the claimed scopes in the present invention.

DESCRIPTION OF THE INVENTION IN DETAIL

The following preparation examples are used to further illustrate the method for preparing the formula (I) provided in the present invention, but not to limit it.

Example 1

Preparation of 3-bromo-N-(2-methyl-4-chloro-6-(methylcarbamoyl)phenyl)-1-(3-chloro-2-pyridinyl)-1H-pyrazole-5-carboxamide (Compound 13 in Table 1)

(1) Synthesis of ethyl 1-(3-chloro-2-pyridinyl)-3-oxopyrazolidine-5-carboxylate

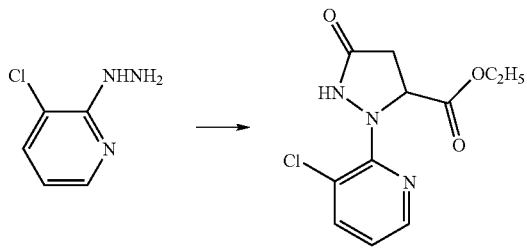

To a 1000 mL flask, anhydrous ethanol (300 mL), sodium ethoxide (16.97 g, 0.249 mol) and 3-chloro-2-hydrazinylpyridine (30.47 g, 98%, 0.21 mol) were added. The reaction mixture was heated to reflux for 5 minutes. Diethyl maleate (36.0 g, 0.31 mol) was added dropwise and heated to reflux for 10 minutes. After being cooled to 65° C., the reaction mixture was neutralized with glacial acetic acid (45.36 g, 0.42 mol) and then diluted with 300 mL water. The reaction mixture was cooled down to room temperature, solid is separated to be filtered, washed with 40% aqueous solution of ethanol (3×50 mL) and dried to give ethyl 1-(3-chloro-2-pyridinyl)-3-oxopyrazolidine-5-carboxylate (31.03 g) as an orange solid in 52% yield. HPLC area normalization method content is 94% (Analytical condition: chromatographic column: ZORBAX Eclipse XDB-C8 4.6×150 mm 5 μm, mobile phase:the ratio of acetonitrile to water is 70:30).

$^1$H NMR (300 MHz, DMSO): 8.289-8.269 (q, 1H), 7.956-7.190 (q, 1H), 7.231-7.190 (q, 1H), 4.862-4.816 (q, 1H), 4.236-4.165 (q, 2H), 2.967-2.879 (q, 1H), 2.396-2.336 (q, 1H), 1.250-1.202 (t, 3H).

(2) Synthesis of ethyl 3-bromo-1-(3-chloro-2-pyridinyl)-4,5-dihydro-1H-pyrazole-5-carboxylate

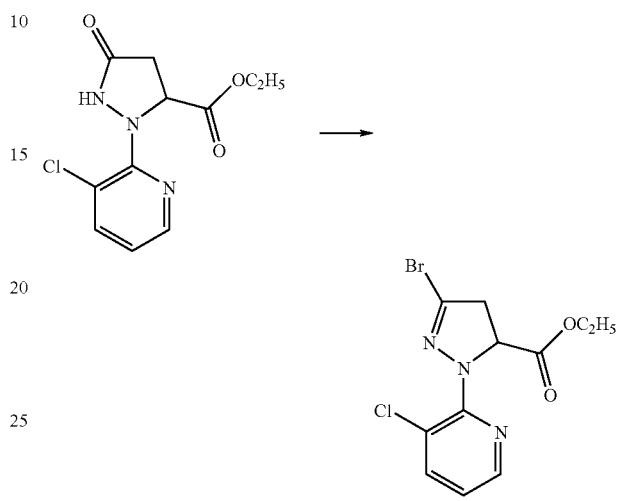

To a 500 mL flask, acetonitrile (200 mL), ethyl 1-(3-chloro-2-pyridinyl)-3-oxopyrazolidine-5-carboxylate (21.28 g, 94%, 74.17 mmol) and phosphoryl bromide (14.88 g, 51.92 mmol) were added. The reaction mixture was heated to reflux for 2 hours. 150 mL solvent was distilled from the reaction mixture. The concentrated reaction mixture was added to the mixture of sodium carbonate (10.56 g, 155.7 mmol) and water (40 mL). The reaction mixture was stirred for 20 minutes until no more gas released, and then diluted with dichloromethane (100 mL), stirred for 50 minutes. The mixture was extracted with dichloromethane (3×200 mL). The combined organic layers were washed with water, dried over anhydrous magnesium sulfate, and concentrated by rotary evaporator to give ethyl 3-bromo-1-(3-chloro-2-pyridinyl)-4,5-dihydro-1H-pyrazole-5-carboxylate (25.73 g) as a amber oil in 97% yield. HPLC area normalization method content is 93% (Analytical condition: chromatographic column: ZORBAX Eclipse XDB-C8 4.6×150 mm 5 μm, mobile phase:the ratio of acetonitrile to water is 70:30).

$^1$H NMR: 8.093-8.073 (q, 1H), 7.681-7.650 (q, 1H), 6.892-6.851 (q, 1H), 5.293-5.224 (q, 1H), 4.220-4.150 (q, 2H), 3.502-3.404 (q, 1H), 3.291-3.202 (q, 1H), 1.226-1.179 (t, 3H).

(3) Synthesis of 3-bromo-1-(3-chloro-2-pyridinyl)-4,5-dihydro-1H-pyrazole-5-carboxylic acid

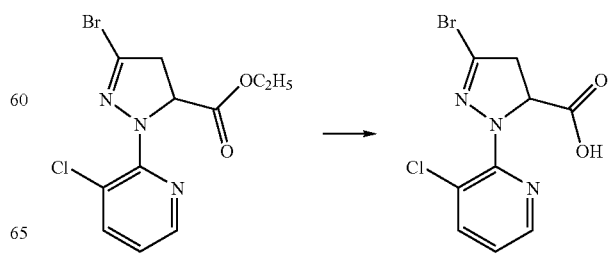

To a 500 mL flask, ethyl 3-bromo-1-(3-chloro-2-pyridinyl)-4,5-dihydro-1H-pyrazole-5-carboxylate (20 g, 93%, 55.92 mmol), ethanol (100 mL) were added. The solution of sodium hydroxide (2.34 g, 58.50 mmol, dissolved into water (100 mL)) was added dropwise. After being stirred for 2 hours at room temperature, the reaction mixture was concentrated by rotary evaporator to remove ethanol. Aqueous solution was extracted with ethyl acetate (30 mL) and acidified with concentrated hydrochloric acid to pH=3. Then aqueous solution was extracted with ethyl acetate (3×100 mL) again. The organic layers were washed with saturated brine (100 mL), dried over anhydrous magnesium sulfate and concentrated by rotary evaporator to give 3-bromo-1-(3-chloro-2-pyridinyl)-4,5-dihydro-1H-pyrazole-5-carboxylic acid (16.67 g) as a yellow solid in 92% yield. HPLC area normalization method content is 94% (Analytical condition: chromatographic column: ZORBAX Eclipse XDB-C84.6×150 mm 5 μm, mobile phase:the ratio of acetonitrile to water is 70:30).

$^1$H NMR (300 MHz, CDCl$_3$) δ (ppm): 9.376 (br s, 1H), 8.106 (dd, 1H), 7.750 (dd, 1H), 6.957 (dd, 1H), 5.186 (dd, 1H), 3.798 (dd, 1H), 3.423 (dd, 1H).

(4) Synthesis of 3-bromo-1-(3-chloro-2-pyridinyl)-1H-pyraole-5-carbonyl chloride

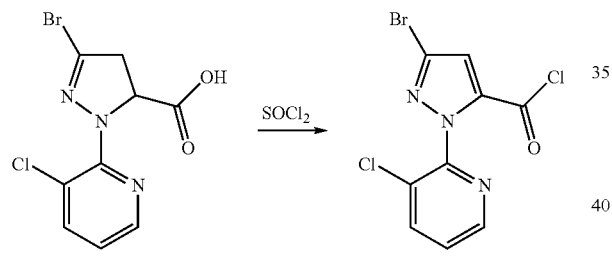

To a 500 mL flask, 3-bromo-1-(3-chloro-2-pyridinyl)-4,5-dihydro-1H-pyrazole-5-carboxylic acid (12 g, 94%, 37.04 mmol), toluene (150 mL) and thionyl dichloride (22.04 g, 185.20 mmol) were added. After being stirred for 10 minutes at room temperature, the reaction mixture was heated to reflux. And the gas of hydrogen chloride produced was absorbed by water to obtain the hydrochloric acid (the hydrochloric acid could be used in the neutralization reaction for preparing 3-bromo-1-(3-chloro-2-pyridinyl)-4,5-dihydro-1H-pyrazole-5-carboxylic acid). After refluxing for 1 hour, the reaction mixture was concentrated under vacuum to give the product (11.88 g) as a brown oil in 98% yield. GC area normalization method content is 98% (Analytical condition: Shimadzu GC, chromatographic column: Chromosorb WAW-DMCS.2M stainless steel column with 5% OV-101, column temperature: 50° C., detector temperature: 200° C., injection temperature: 200° C.).

$^1$H NMR (300 MHz, CDCl$_3$) δ (ppm): 8.510 (dd, 1H), 7.948 (d, 1H), 7.489 (dd, 1H), 7.301 (s, 1H). MS: (m/z) 319 (M$^+$), 284 (M$^+$-Cl).

(5) Synthesis of 3-bromo-N-(4-chloro-2-methyl-6-(methylcarbamoyl)phenyl)-1-(3-chloro-2-pyridinyl)-1H-pyrazole-5-carboxamide (Compound 13 in Table 1)

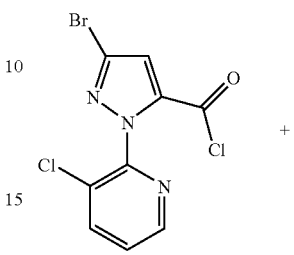

+

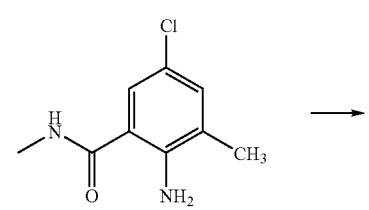

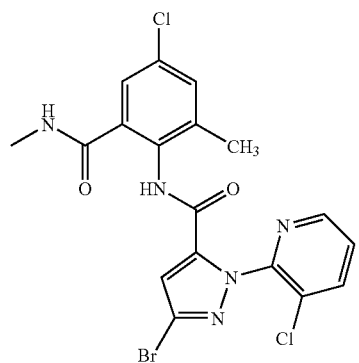

To a 250 mL flask, 2-amino-5-chloro-N,3-dimethylbenzamide (8.13 g, 94%, 38.47 mmol), acetonitrile (70 mL), 3-bromo-1-(3-chloro-2-pyridinyl)-1H-pyrazole-5-carbonyl chloride (12.60 g, 98%, 38.47 mmol) were added. After being stirring for 10 minutes at room temperature, the reaction mixture was heated to reflux, and the gas of hydrogen chloride produced in the reaction was absorbed by water to obtain the hydrochloric acid (the hydrochloric acid could be used in the neutralization reaction for preparing 3-bromo-1-(3-chloro-2-pyridinyl)-4,5-dihydro-1H-pyrazole-5-carboxylic acid). After refluxing for 1 hour, the reaction mixture was poured into saturated sodium bicarbonate solution, and the precipitate was isolated via filtration and dried to give the product (17.81 g) in 92% yield. HPLC area normalization method content is 96%.

(The total yield of the preparation of 3-bromo-N-(4-chloro-2-methyl-6-(methylcarbamoyl)phenyl)-1-(3-chloro-2-pyridinyl)-1H-pyrazole-5-carboxamide through three steps calculated by ethyl 3-bromo-1-(3-chloro-2-pyridinyl)-4,5-dihydro-1H-pyrazole-5-carboxylate is 83%).

Example 2

Preparation of 3-bromo-N-(4-cyano-2-methyl-6-(methylcarbamoyl)phenyl)-1-(3-chloro-2-pyridinyl)-1H-pyrazole-5-carboxamide (Compound 23 in Table 1)

(1) Synthesis of pentyl 2-(3-chloro-2-pyridinyl)-3-oxopyrazolidine-5-carboxylate

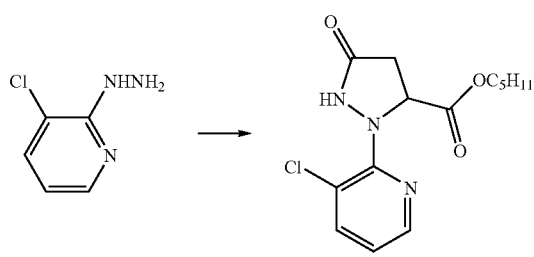

To a three-necked flask, pentan-1-ol (150 mL) was added. And the sodium (3.0 g, 0.13 mol) was added partially. The reaction mixture was heated to reflux for 30 minutes at 100° C. When the sodium reacted completely, the mixture was cooled to 60° C. Then 3-chloro-2-hydrazinylpyridine (12.75 g, 98%, 0.09 mol) were added and reacted for 30 minutes. The dimethyl maleate (12.50 g, 0.11 mol) was added dropwise. The reaction mixture was heated to reflux for 10 minutes. After cooled to 65° C., the reaction mixture was neutralized with glacial acetic acid (13.04 g, 0.23 mol) and diluted with water (300 mL). After cooled to room temperature, solid is separated out to be filtered and, washed with 40% aqueous solution of ethanol (3×50 mL) and dried to give pentyl 2-(3-chloro-2-pyridinyl)-5-oxopyrazolidine-3-carboxylate (12.00 g) as a orange solid in 42% yield. HPLC area normalization method content is 95% (Analytical condition: chromatographic column: ZORBAX Eclipse XDB-C8 4.6×150 mm 5 μm, mobile phase:the ratio of acetonitrile to water is 70:30).

$^1$H NMR (300 MHz, DMSO): 8.214 (dd, 1H), 7.679 (dd, 1H), 7.016 (dd, 1H), 5.240 (dd, 1H), 4.205 (t, 2H), 3.109 (dd, 1H), 2.758 (dd, 1H), 1.694-1.602 (m, 2H), 1.358-1.288 (m, 4H), 0.896 (t, 3H).

(2) Synthesis of pentyl 3-bromo-1-(3-chloro-2-pyridinyl)-4,5-dihydro-1H-pyrazole-5-carboxylate

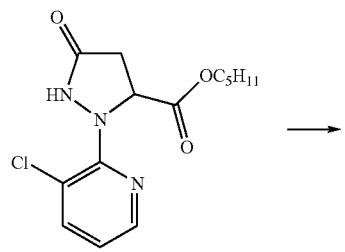

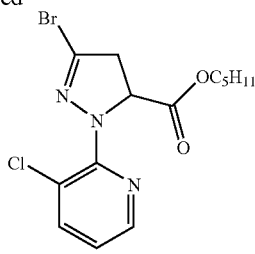

To a 250 mL flask, acetonitrile (80 mL), pentyl 2-(3-chloro-2-pyridinyl)-3-oxopyrazolidine-5-carboxylate (8.44 g, 95%, 25.72 mmol) and phosphoryl bromide (5.2 g, 18.00 mmol) were added. The reaction mixture was heated to reflux for 2 hours. The reaction mixture was distilled to remove 60 mL solvent. The concentrated reaction mixture was added to the mixture of sodium carbonate (8.40 g, 96 mmol) and water (50 mL). The reaction mixture was stirred for 20 minutes until no more gas released. The reaction mixture was diluted with dichloromethane (200 mL), stirred for 50 minutes and extracted with dichloromethane (3×100 mL) again. The combined organic layers were washed with water, dried over anhydrous magnesium sulfate and concentrated by rotary evaporator to give pentyl 3-bromo-1-(3-chloro-2-pyridinyl)-4,5-dihydro-1H-pyrazole-5-carboxylate (7.28 g) as an amber oil in 73% yield. HPLC area normalization method content is 97% (Analytical condition: chromatographic column: ZORBAX Eclipse XDB-C8 4.6×150 mm 5 μm, mobile phase:the ratio of acetonitrile and water is 70:30).

$^1$H NMR (300 MHz, DCl$_3$): 8.083 (dd, 1H), 7.674 (dd, 1H), 6.877 (dd, 1H), 5.283 (dd, 1H), 4.109 (t, 2H), 3.461 (dd, 1H), 3.266 (dd, 1H), 1.577-1.499 (m, 2H), 1.291-1.150 (m, 4H), 0.845 (t, 3H).

(3) Synthesis of 3-bromo-1-(3-chloro-2-pyridinyl)-4,5-dihydro-1H-pyrazole-5-carboxylic acid

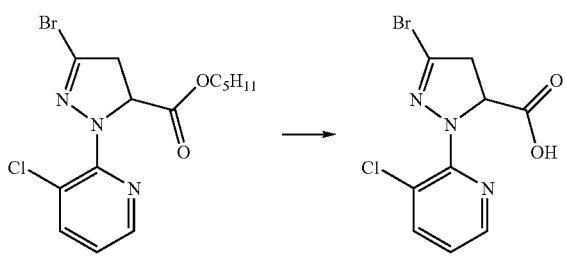

To a 100 mL flask, pentyl 3-bromo-1-(3-chloro-2-pyridinyl)-4,5-dihydro-1H-pyrazole-5-carboxylate (5.00 g, 97%, 12.94 mmol), ethanol (30 mL), water (30 mL) and sodium hydroxide (0.52 g, 12.94 mmol) were added. The reaction mixture was stirred for 6 hours at room temperature. The reaction mixture was concentrated by rotary evaporator to remove ethanol. Then water (250 mL) was added. Aqueous solution was extracted with ethyl acetate (100 mL), acidified with concentrated hydrochloric acid to pH=2 and extracted with dichloromethane (3×200 mL) again. The combined organic layers were dried over anhydrous magnesium sulfate and concentrated by rotary evaporator to give 3-bromo-1-(3-chloro-2-pyridinyl)-1H-pyrazole-5-carboxylic acid (3.60 g) as a white solid in 90% yield. HPLC area normalization method content is 98% (Analytical condition: chromatographic column: ZORBAX Eclipse XDB-C8 4.6×150 mm 5 μm, mobile phase:the ratio of acetonitrile to water is 70:30).

(4) Synthesis of 3-bromo-1-(3-chloro-2-pyridinyl)-1H-pyrazole-5-carbonyl chloride

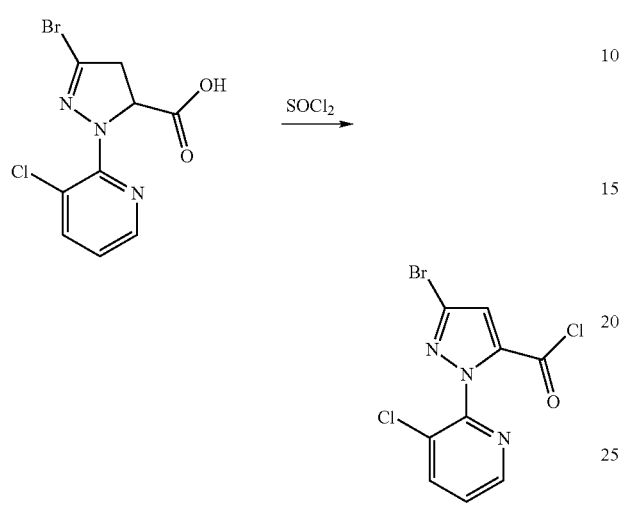

To a 500 mL flask, 3-bromo-1-(3-chloro-2-pyridinyl)-4,5-dihydro-1H-pyrazole-5-carboxylic acid (12 g, 94%, 37.04 mmol, product of example 1 (3)), toluene (100 mL) and thionyl dichloride (22.04 g, 185.20 mmol) were added. After being stirred for 10 minutes at room temperature, the reaction mixture was heated to reflux and the gas of hydrogen chloride produced in the reaction was absorbed by water to obtain the hydrochloric acid (The hydrochloric acid could be used in the neutralization reaction of preparing 3-bromo-1-(3-chloro-2-pyridinyl)-4,5-dihydro-1H-pyrazole-5-carboxylic acid). After refluxing for 1 hour, the reaction mixture was concentrated under vacuum to give the product (11.88 g) as a henna oil in 98% yield. GC area normalization method content is 98%. (Analytical condition: Shimadzu GC, chromatographic column: Chromosorb WAW-DMCS.2M stainless steel column with 5% OV-101, column temperature: 50° C., detector temperature: 200° C., injection temperature: 200° C.).

$^1$H NMR (300 MHz, CDCl3) δ (ppm): 8.510 (dd, 1H), 7.948 (d, 1H), 7.489 (dd, 1H), 7.301 (s, 1H). MS: (m/z) 319 (M$^+$), 284 (M$^+$-Cl).

(5) Synthesis of 3-bromo-1-(3-chloro-2-pyridinyl)-N-(4-cyano-2-methyl-6-(methylcarbamoyl)phenyl)-1H-pyrazole-5-carboxamide (Compound 23 in Table 1)

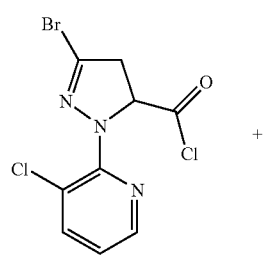 +

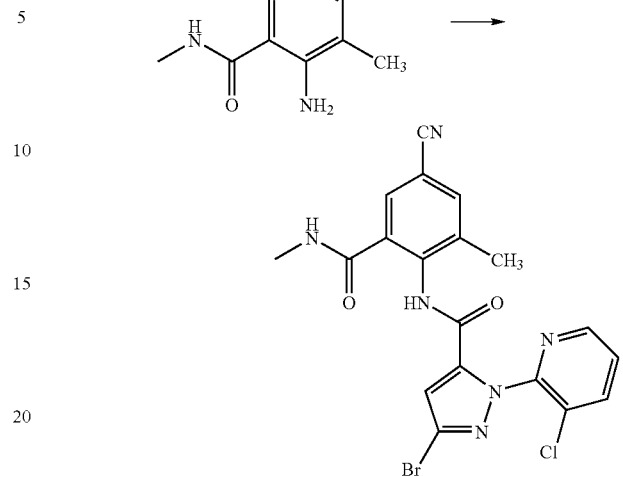

To a 100 mL flask, 2-amino-5-cyano-N,3-dimethylbenzamide (2.30 g, 95%, 11.66 mmol), acetonitrile (50 mL), 3-bromo-1-(3-chloro-2-pyridinyl)-1H-pyrazole-5-carbonyl chloride (3.81 g, 98%, 11.66 mmol) were added. After being stirred for 10 minutes at room temperature, the reaction mixture was heated to reflux and the gas of hydrogen chloride produced in the reaction was absorbed by water to obtain the hydrochloric acid (The hydrochloric acid could be used in the neutralization reaction of preparing 3-bromo-1-(3-chloro-2-pyridinyl)-4,5-dihydro-1H-pyrazole-5-carboxylic acid). After refluxing for 1 hour, the reaction mixture was poured into saturated sodium bicarbonate solution. The precipitate was isolated via filtration and dried to give the product (5.58 g) in 93% yield. HPLC area normalization method content is 92%.

(The total yield of preparing 3-bromo-1-(3-chloro-2-pyridinyl)-N-(4-cyano-2-methyl-6-(methylcarbamoyl)phenyl)-1H-pyrazole-5-carboxamide through three steps calculated by pentyl 3-bromo-1-(3-chloro-2-pyridinyl)-4,5-dihydro-1H-pyrazole-5-carboxylate is 82%).

The following comparison examples were carried out according to the literature of WO03/015519 A1 and WO2006/062978 A1.

Comparison Example 1

Synthesis of 3-bromo-N-(4-chloro-2-methyl-6-(methylcarbamoyl)phenyl)-1-(3-chloro-2-pyridinyl)-1H-pyrazole-5-carboxamide (1) Synthesis of ethyl 3-bromo-1-(3-chloro-2-pyridinyl)-1H-pyrazole-5-carboxylate

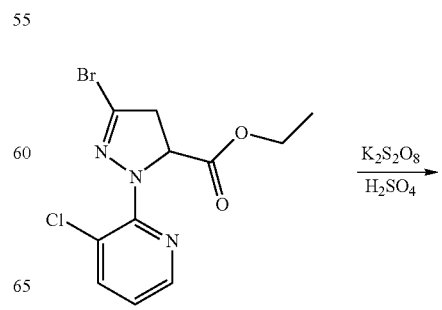

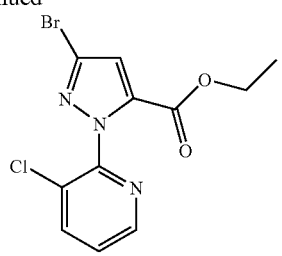

To a 500 mL flask, ethyl 3-bromo-1-(3-chloro-2-pyridinyl)-4,5-dihydro-1H-pyrazole-5-carboxylate (22.22 g, 90%, 60 mmol), potassium persulfate (25.92 g, 96 mmol) and acetonitrile (180 mL) were added. The reaction mixture was stirred at room temperature. The concentrated sulfuric acid (12 g) was added dropwise. After added completely, the reaction mixture was heated to reflux for 2 hours. The mixture was concentrated by rotary evaporator to remove most acetonitrile. Water (100 mL) was added and then the mixture was extracted with ethyl acetate (3×150 mL). The combined organic layers were washed with saturated sodium bicarbonate solution (100 mL) and saturated brine (100 mL), dried over anhydrous magnesium sulfate and concentrated by rotary evaporator to give the product (21.50 g) as a yellow solid in 90% yield. HPLC area normalization method content is 83%.

$^1$H NMR (300 MHz, CDCl$_3$): 8.522-8.501 (q, 1H), 7.927-7.895 (q, 1H), 7.465-7.424 (q, 1H), 7.034 (s, 1H), 4.262-4.190 (q, 2H), 1.240-1.192 (t, 3H).

(2) Synthesis of 3-bromo-1-(3-chloro-2-pyridinyl)-1H-pyrazole-5-carboxylic acid

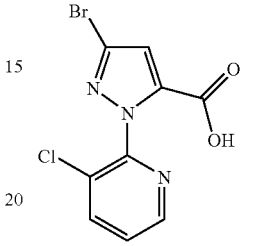

To a 500 mL flask, ethyl 3-bromo-1-(3-chloropyridin-2-yl)-1H-pyrazole-5-carboxylate (22.00 g, 83%, 55.23 mmol) and ethanol (100 mL) were added. The sodium hydroxide solution (2.20 g, 55.23 mmol, dissolved into water (100 mL)) was added dropwise. After being stirred for 2 hours at room temperature, the reaction mixture was concentrated by rotary evaporator to remove ethanol. The residue was extracted with ethyl acetate (30 mL) and the aqueous layer was acidified with concentrated hydrochloric acid to pH=3. Then the aqueous solution was extracted with ethyl acetate (3×100 mL) again. The combined organic layers were washed with saturated brine (100 mL), dried over anhydrous magnesium sulfate and concentrated by rotary evaporator to give the product (15.51 g) as a light yellow solid in 91% yield. HPLC area normalization method content is 98%.

$^1$H NMR (300 MHz, CDCl$_3$) δ (ppm) 9.376 (br s, 1H), 8.106 (dd, 1H), 7.750 (dd, 1H), 6.957 (dd, 1H), 5.186 (dd, 1H), 3.798 (dd, 1H), 3.423 (dd, 1H).

(3) Synthesis of 3-bromo-N-(4-chloro-2-methyl-6-(methylcarbamoyl)phenyl)-1-(3-chlro-2-pyridinyl)-1H-pyrazole-5-carboxamide (Compound 13 in Table 1)

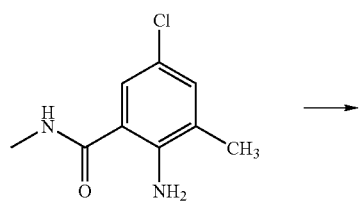

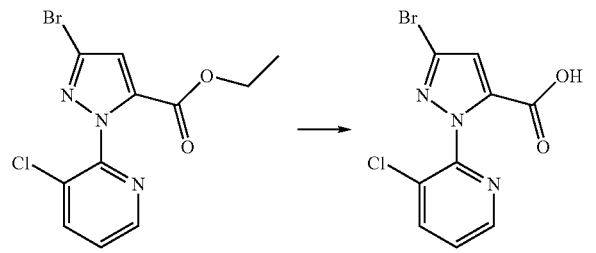

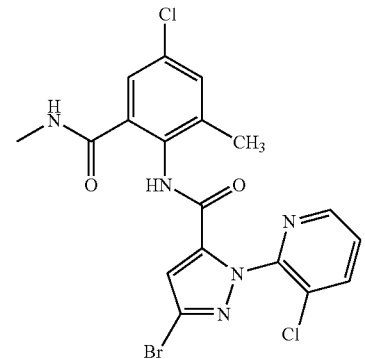

To a 100 mL flask, 2-amino-5-chloro-N,3-dimethylbenzamide (8.58 g, 94%, 40.62 mmol), acetonitrile (50 mL), 3-bromo-1-(3-chloro-2-pyridinyl)-1H-pyrazole-5-carboxylic acid (12.0 g, 98%, 38.68 mmol) and pyridine (7.95 g, 100.57 mmol) were added. The reaction mixture was cooled to −5° C., and methanesulfonyl chloride (5.32 g, 46.44 mmol) was added dropwise in 10 minutes. The reaction mixture was held at −5° C. to 0° C. for 1 hour. Then the reaction mixture was reacted for 3 hour at room temperature. Water (18 mL) was added dropwise. The reaction mixture was stirred for 10 minutes at room temperature. The precipitate was isolated via filtration and dried to give the product (18.30 g) as a brown solid in 93% yield. HPLC area normalization method content is 95%.

(The total yield of preparing 3-bromo-N-(4-chloro-2-methyl-6-(methylcarbamoyl)phenyl)-1-(3-chloro-2-pyridinyl)-1H-pyrazole-5-carboxamide through three steps calculated by ethyl 3-bromo-1-(3-chloro-2-pyridinyl)-4,5-dihydro-1H-pyrazole-5-carboxylate is 76%.)

Comparison Example 2

Synthesis of 3-bromo-1-(3-chloro-2-pyridinyl)-N-(4-cyano-2-methyl-6-(methylcarbamoyl)phenyl)-1H-pyrazole-5-carboxamide (Compound 23 in Table 1)

(1) Synthesis of ethyl 3-bromo-1-(3-chloro-2-pyridinyl)-1H-pyrazole-5-carboxylate

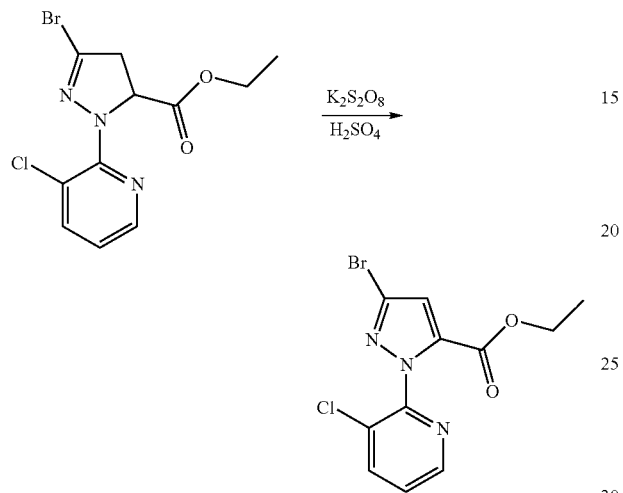

To a 500 mL flask, ethyl 3-bromo-1-(3-chloro-2-pyridinyl)-4,5-dihydro-1H-pyrazole-5-carboxylate (20.00 g, 90%, 54.12 mmol), potassium persulfate (23.40 g, 86.60 mmol) and acetonitrile (180 mL) were added. The reaction mixture was stirred at room temperature. The sulfuric acid (10.82 g, 108.24 mmol) was added dropwise slowly. After added completely, the reaction mixture was heated to reflux for 2 hours. The reaction mixture was concentrated by rotary evaporator to remove most acetonitrile. Water (100 mL) was added and the reaction mixture was extracted with ethyl acetate (3×150 mL). The combined organic layers were washed with saturated sodium bicarbonate solution (100 mL) and saturated brine (100 mL), dried over anhydrous magnesium sulfate and concentrated by rotary evaporator to give the product (18.73 g) as a yellow solid in 89% yield. HPLC area normalization method content is 85%.

$^1$H NMR (300 MHz, CDCl$_3$): 8.522-8.501 (q, 1H), 7.927-7.895 (q, 1H), 7.465-7.424 (q, 1H), 7.034 (s, 1H), 4.262-4.190 (q, 2H), 1.240-1.192 (t, 3H).

(2) Synthesis of 3-bromo-1-(3-chloro-2-pyridinyl)-1H-pyrazole-5-carboxylic acid

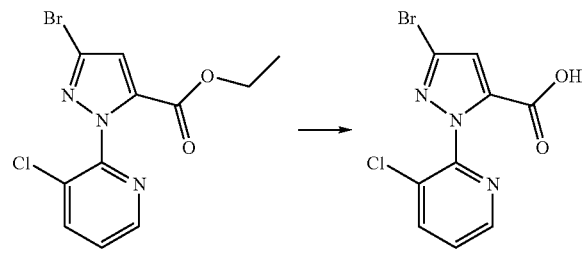

To a 500 mL flask, ethyl 3-bromo-1-(3-chloro-2-pyridinyl)-1H-pyrazole-5-carboxylate (15.00 g, 85%, 38.57 mmol) and ethanol (80 mL) were added. Sodium hydroxide solution (1.54 g, 38.57 mmol, dissolved in water (80 mL)) were added dropwise. The reaction mixture was stirred at room temperature for 2 hours. The mixture was concentrated by rotary evaporator to remove ethanol. The residue was extracted with ethyl acetate (30 mL) and acidified with concentrated hydrochloric acid to pH=3. Aqueous solution was extracted with ethyl acetate (3×100 mL) again. The combined organic layers were washed with saturated brine (100 mL), dried over anhydrous magnesium sulfate and concentrated by rotary evaporator to give the product (10.83 g) as a yellow solid in 91% yield. HPLC area normalization method content is 98%.

$^1$H NMR (300 MHz, CDCl$_3$) δ (ppm): 9.376 (br s, 1H), 8.106 (dd, 1H), 7.750 (dd, 1H), 6.957 (dd, 1H), 5.186 (dd, 1H), 3.798 (dd, 1H), 3.423 (dd, 1H).

(3) Synthesis of compound 3-bromo-1-(3-chloro-2-pyridinyl)-N-(4-cyano-2-methyl-6-(methylcarbamoyl)phenyl)-1H-pyrazole-5-carboxamid (Compound 23 in Table 1)

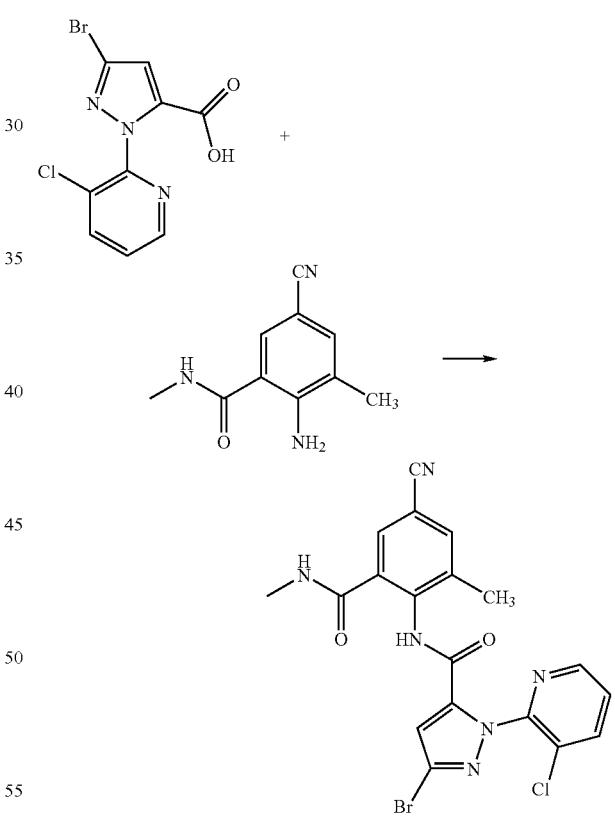

To a 100 mL flask, 3-bromo-1-(3-chloro-2-pyridinyl)-1H-pyrazole-5-carboxylic acid (10.00 g, 98%, 32.40 mmol), 2-amino-5-cyano-N,3-dimethylbenzamide (6.77 g, 95%, 34.00 mmol), acetonitrile (50 mL) and pyridine (9.21 g, 116.64 mmol) was added. The reaction mixture was cooled to −5° C. Methanesulfonyl chloride (5.19 g, 45.36 mmol) was added dropwise in 10 minutes, and then maintaining the reaction mixture at −5° C. to 0° C. for 1 hour, then warmed to room temperature and reacted for 3 hours. Water (18 mL) was added dropwise. The reaction mixture was stirred for 1 hour at room temperature. The precipitate was isolated via filtration and dried to give the product (15.34 g) as a brown solid in 92% yield. HPLC area normalization method content is 92%.

(The total yield of preparing 3-bromo-1-(3-chloro-2-pyridinyl)-N-(4-cyano-2-methyl-6-(methylcarbamoyl)phenyl)-1H-pyrazole-5-carboxamide through three steps calculated by ethyl 3-bromo-1-(3-chloro-2-pyridinyl)-4,5-dihydro-1H-pyrazole-5-carboxylate is 75%).

The phenylcarboxamides of formula (I) can be prepared according to the method provided in the present invention. The structures of some representative compounds of formula (I) are showed in Table 1.

TABLE 1

The structures of some representative compounds of formula (I)

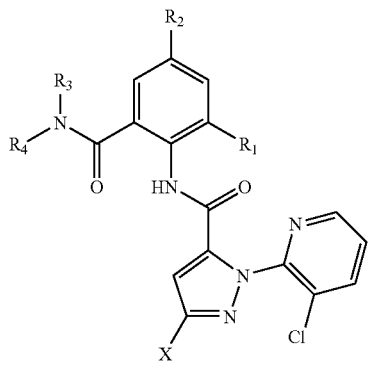

| Compound | $R_1$ | $R_2$ | $R_3$ | $R_4$ | X |
|---|---|---|---|---|---|
| 1 | $CH_3$ | Cl | H | H | Br |
| 2 | Cl | Cl | H | H | Br |
| 3 | $CH_3$ | Br | H | H | Br |
| 4 | Cl | Br | H | H | Br |
| 5 | $CH_3$ | F | H | H | Cl |
| 6 | Cl | F | H | H | Cl |
| 7 | $CH_3$ | Cl | H | H | Cl |
| 8 | Cl | Cl | H | H | Cl |
| 9 | $CH_3$ | Br | H | H | Cl |
| 10 | Cl | Br | H | H | Cl |
| 11 | $CH_3$ | F | H | $CH_3$ | Br |
| 12 | Cl | F | H | $CH_3$ | Br |
| 13 | $CH_3$ | Cl | H | $CH_3$ | Br |
| 14 | F | Cl | H | $CH_3$ | Br |
| 15 | Cl | Cl | H | $CH_3$ | Br |
| 16 | Br | Cl | H | $CH_3$ | Br |
| 17 | CN | Cl | H | $CH_3$ | Br |
| 18 | $CH_3$ | Br | H | $CH_3$ | Br |
| 19 | F | Br | H | $CH_3$ | Br |
| 20 | Cl | Br | H | $CH_3$ | Br |
| 21 | Br | Br | H | $CH_3$ | Br |
| 22 | CN | Br | H | $CH_3$ | Br |
| 23 | $CH_3$ | CN | H | $CH_3$ | Br |
| 24 | F | CN | H | $CH_3$ | Br |
| 25 | Cl | CN | H | $CH_3$ | Br |
| 26 | CN | CN | H | $CH_3$ | Br |
| 27 | Br | CN | H | $CH_3$ | Br |
| 28 | $CH_3$ | F | H | $CH_3$ | Cl |
| 29 | Cl | F | H | $CH_3$ | Cl |
| 30 | $CH_3$ | Cl | H | $CH_3$ | Cl |
| 31 | F | Cl | H | $CH_3$ | Cl |
| 32 | Cl | Cl | H | $CH_3$ | Cl |
| 33 | Br | Cl | H | $CH_3$ | Cl |
| 34 | CN | Cl | H | $CH_3$ | Cl |
| 35 | $CH_3$ | Br | H | $CH_3$ | Cl |
| 36 | F | Br | H | $CH_3$ | Cl |
| 37 | Cl | Br | H | $CH_3$ | Cl |
| 38 | Br | Br | H | $CH_3$ | Cl |
| 39 | CN | Br | H | $CH_3$ | Cl |
| 40 | $CH_3$ | CN | H | $CH_3$ | Cl |
| 41 | F | CN | H | $CH_3$ | Cl |
| 42 | Cl | CN | H | $CH_3$ | Cl |
| 43 | Br | CN | H | $CH_3$ | Cl |
| 44 | CN | CN | H | $CH_3$ | Cl |
| 45 | $CH_3$ | Cl | H | $-CH_2CH_3$ | Br |
| 46 | Cl | Cl | H | $-CH_2CH_3$ | Br |
| 47 | $CH_3$ | CN | H | $-CH_2CH_3$ | Br |
| 48 | Cl | CN | H | $-CH_2CH_3$ | Br |
| 49 | $CH_3$ | Cl | H | $-CH_2CH_3$ | Cl |
| 50 | Cl | Cl | H | $-CH_2CH_3$ | Cl |
| 51 | $CH_3$ | CN | H | $-CH_2CH_3$ | Cl |
| 52 | Cl | CN | H | $-CH_2CH_3$ | Cl |
| 53 | $CH_3$ | F | H | $-CH(CH_3)_2$ | Br |
| 54 | Cl | F | H | $-CH(CH_3)_2$ | Br |
| 55 | $CH_3$ | Cl | H | $-CH(CH_3)_2$ | Br |
| 56 | Cl | Cl | H | $-CH(CH_3)_2$ | Br |
| 57 | Br | Cl | H | $-CH(CH_3)_2$ | Br |
| 58 | $CH_3$ | Br | H | $-CH(CH_3)_2$ | Br |
| 59 | Cl | Br | H | $-CH(CH_3)_2$ | Br |
| 60 | Br | Br | H | $-CH(CH_3)_2$ | Br |
| 61 | $CH_3$ | CN | H | $-CH(CH_3)_2$ | Br |
| 62 | Cl | CN | H | $-CH(CH_3)_2$ | Br |
| 63 | Br | CN | H | $-CH(CH_3)_2$ | Br |
| 64 | $CH_3$ | F | H | $-CH(CH_3)_2$ | Cl |
| 65 | Cl | F | H | $-CH(CH_3)_2$ | Cl |
| 66 | $CH_3$ | Cl | H | $-CH(CH_3)_2$ | Cl |
| 67 | Cl | Cl | H | $-CH(CH_3)_2$ | Cl |
| 68 | Br | Cl | H | $-CH(CH_3)_2$ | Cl |
| 69 | $CH_3$ | Br | H | $-CH(CH_3)_2$ | Cl |
| 70 | Cl | Br | H | $-CH(CH_3)_2$ | Cl |
| 71 | Cl | Br | H | $-CH(CH_3)_2$ | Cl |
| 72 | $CH_3$ | CN | H | $-CH(CH_3)_2$ | Cl |
| 73 | Cl | CN | H | $-CH(CH_3)_2$ | Cl |
| 74 | Br | CN | H | $-CH(CH_3)_2$ | Cl |
| 75 | $CH_3$ | Cl | H | cyclopropyl | Br |
| 76 | Cl | Cl | H | cyclopropyl | Br |
| 77 | Br | Cl | H | cyclopropyl | Br |
| 78 | $CH_3$ | Br | H | cyclopropyl | Br |
| 79 | Cl | Br | H | cyclopropyl | Br |
| 80 | $CH_3$ | CN | H | cyclopropyl | Br |
| 81 | Cl | CN | H | cyclopropyl | Br |
| 82 | $CH_3$ | Cl | H | cyclopropyl | Cl |

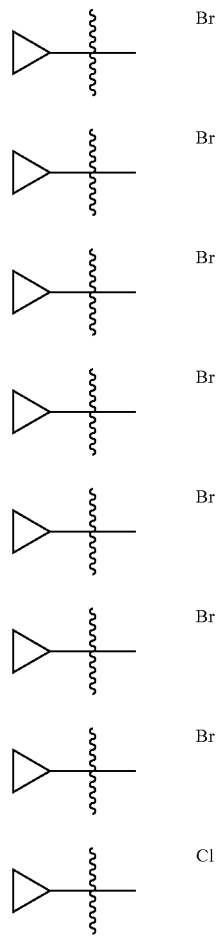

TABLE 1-continued

| # | | | | | |
|---|---|---|---|---|---|
| 83 | Cl | Cl | H | 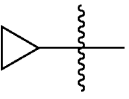 | Cl |
| 84 | CH₃ | CN | H | 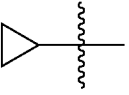 | Cl |
| 85 | Cl | CN | H | 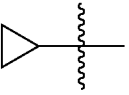 | Cl |
| 86 | CH₃ | Cl | H | 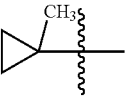 | Br |
| 87 | Cl | Cl | H | 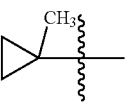 | Br |
| 88 | Br | Cl | H | 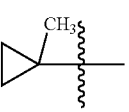 | Br |
| 89 | CH₃ | Br | H | 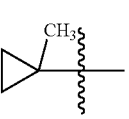 | Br |
| 90 | Cl | Br | H | 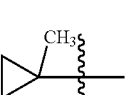 | Br |
| 91 | CH₃ | CN | H | 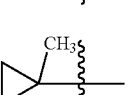 | Br |
| 92 | Cl | CN | H | 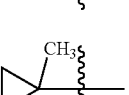 | Br |
| 93 | CH₃ | Cl | H | 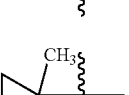 | Cl |
| 94 | Cl | Cl | H | 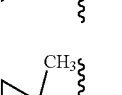 | Cl |
| 95 | CH₃ | CN | H | 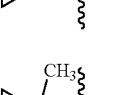 | Cl |
| 96 | Cl | CN | H | 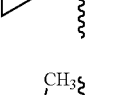 | Cl |
| 97 | CH₃ | Cl | H | 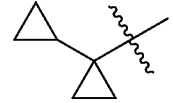 | Br |
| 98 | Cl | Cl | H |  | Br |
| 99 | CH₃ | Cl | H | 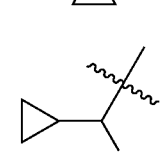 | Br |
| 100 | Cl | Cl | H | 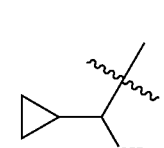 | Br |
| 101 | CH₃ | Cl | H | 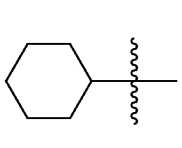 | Br |
| 102 | Cl | Cl | H | 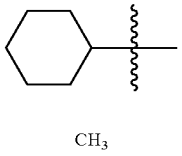 | Br |
| 103 | CH₃ | Cl | CH₃ | CH₃ | Br |
| 104 | Cl | Cl | CH₃ | CH₃ | Br |
| 105 | CH₃ | Br | CH₃ | CH₃ | Br |
| 106 | Cl | Br | CH₃ | CH₃ | Br |
| 107 | CH₃ | CN | CH₃ | CH₃ | Br |
| 108 | Cl | CN | CH₃ | CH₃ | Br |
| 109 | CH₃ | Cl | CH₃ | CH₃ | Br |
| 110 | Cl | Cl | CH₃ | CH₃ | Br |
| 111 | CH₃ | Br | CH₃ | CH₃ | Br |
| 112 | Cl | Br | CH₃ | CH₃ | Br |
| 113 | CH₃ | CN | CH₃ | CH₃ | Br |
| 114 | Cl | CN | CH₃ | CH₃ | Br |

What is claimed is:

1. A preparation method of phenylcarboxamides as represented by formula (I), the reaction scheme is as follows:

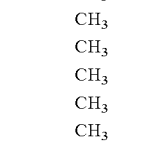

(V)

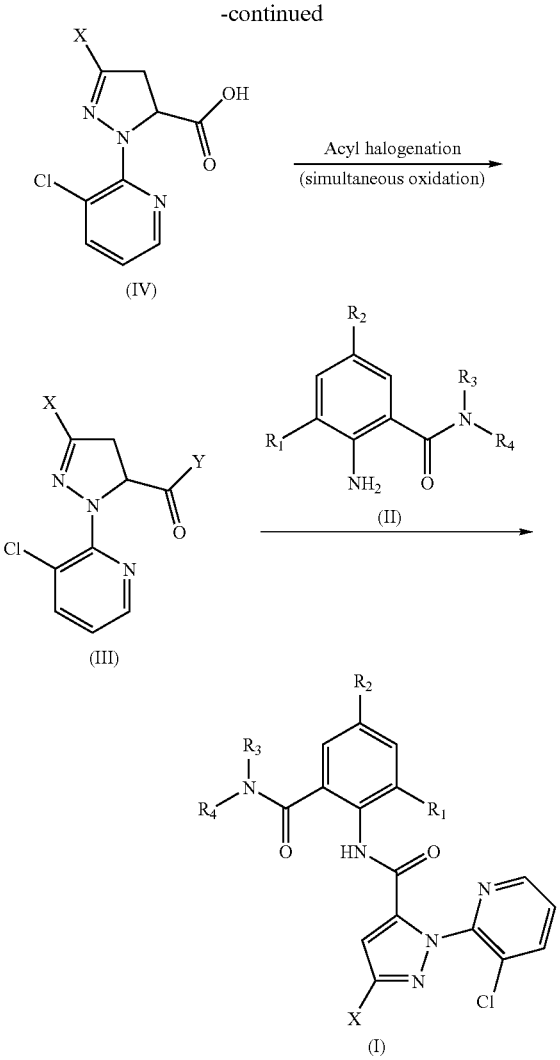

wherein:
R$_1$ is halogen, CN or CH$_3$; R$_2$ is halogen or CN; R$_3$ is H or C$_1$-C$_3$ alkyl; R$_4$ is H, C$_1$-C$_6$ alkyl or C$_3$-C$_6$ cycloalkyl; R$_5$ is C$_1$-C$_{10}$ alkyl, benzyl or C$_3$-C$_5$ alkenyl; X and Y are selected independently Cl or Br;
the reaction steps are as follows:
1) hydrolysis reaction: the 3-halo-1-(3-chloro-2-pyridyl)-4,5-dihydro-1H-pyrazole-5-carboxylate (V) is added into 10 to 500 times moles solvent of water, the mixture of water and alcohol, or the mixture of water and ether, then add 0.8 to 2 times moles of base, at a temperature from −10° C. to boiling point for 0.5 to 48 hours; the carboxylic acid salt is formed, and then acidified to form the 3-halo-1-(3-chloro-2-pyridyl)-4,5-dihydro-1H-pyrazole-5-carboxylic acid of formula (IV); when using the mixture of water and alcohol, or water and ether as solvent, the volume ratio of water to alcohol, or water to ether is 1:0.1-10;

2) acyl halogenation and oxidation reaction: the carboxylic acid of formula (IV) react with 1 to 20 times moles acyl halide reagents in the appropriate solvent to obtain the 3-halo-1-(3-chloro-2-pyridyl)-1H-pyrazole-5-carbonyl halide of formula (III) at a temperature between −10° C. and boiling point for 0.5 to 48 hours for the acyl halogenation and oxidation reaction; the acyl halide reagent is selected from the group consisting of thionyl chloride, phosphorus trichloride, phosphorus tribromide, phosphorus pentachloride or phosphorus pentabromide; the solvent is selected from the group consisting of benzene, toluene, acetonitrile, dioxane, hexane or liquid acyl halide reagents, and the amount of solvent is 5 to 500 times moles larger than that of the acid of formula (IV);

3) condensation reaction: the acyl halide of formula (III) reacts with aniline (II), the molar ratio of which is 1:0.8-1.2, without the presence of acid binding agent in the appropriate solvent to obtain the phenylcarboxamide of formula (I) at a temperature between −10° C. and boiling point for 1 to 10 hours; the solvent is selected from the group consisting of dichloromethane, chloroform, carbon tetrachloride, hexane, benzene, toluene, ethyl acetate, acetonitrile, tetrahydrofuran, dioxane, acetone, butanone or dimethyl sulfoxide, and the amount of solvent is 5 to 500 times moles larger than that of acyl halide of formula (III).

2. The method of claim 1, wherein: in the hydrolysis reaction the molar ratio of the ester to base is 1:1-1.2; temperature is between 10° C. and 50° C.; and the reaction time is 0.5 to 2 hours; the base is the hydroxide or carbonate of the alkaline metal.

3. The method of claim 2, wherein: the base is sodium hydroxide or potassium hydroxide.

4. The method of claim 1, wherein: in the hydrolysis reaction the solvent is selected from the mixture of water and alcohol, or the mixture of water and ether, the volume ratio of water to alcohol, or water to ether is 1:0.5-1.5.

5. The method of claim 1, wherein: in the acyl halogenation and oxidation process, the molar ratio of the acid of formula (IV) to acyl halide is 1:2-5; the temperature is between 50° C. and boiling point; the reaction time is 1 to 10 hours; the solvent is selected from the group consisting of benzene, toluene or hexane.

6. The method of claim 1, wherein: in the condensation reaction, the molar ratio of the acyl halide of formula (III) to the substituted aniline (II) is 1:0.9-1.1; the reaction temperature is between 20° C. and boiling point; the reaction time is 1 to 5 hours; the solvent is toluene or acetonitrile.

* * * * *